(12) United States Patent
Klemm et al.

(10) Patent No.: US 8,132,276 B2
(45) Date of Patent: Mar. 13, 2012

(54) PATIENT SUPPORT APPARATUS

(75) Inventors: Tobias Klemm, Saalfeld (DE); Ludwig Kreischer, Dormitz (DE); Mathias Peters, Tiefengruben (DE); Christian Streitberger, Saalfeld (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/887,540

(22) Filed: Sep. 22, 2010

(65) Prior Publication Data

US 2011/0067179 A1 Mar. 24, 2011

(30) Foreign Application Priority Data

Sep. 24, 2009 (DE) .......................... 10 2009 042 873

(51) Int. Cl.
*A61G 13/06* (2006.01)
(52) U.S. Cl. ............................. 5/601; 379/209; 600/410
(58) Field of Classification Search ............... 5/600–601, 5/611, 614, 616; 378/209; 600/410
See application file for complete search history.

(56) References Cited

U.S. PATENT DOCUMENTS

| 4,567,894 A | * | 2/1986 | Bergman | 600/415 |
| 4,671,728 A | * | 6/1987 | Clark et al. | 414/401 |
| 2006/0167356 A1 | | 7/2006 | Everett et al. | |

FOREIGN PATENT DOCUMENTS

| DE | 4224695 C1 | 1/1994 |
| EP | 0209326 A2 | 1/1987 |

* cited by examiner

*Primary Examiner* — Fredrick Conley

(57) ABSTRACT

A simplify mobile patient support apparatus which is suitable for an examination of a patient by a magnetic resonance tomography system is proposed. A first and second actuation facility and a control facility are used. Depending on the operating state of the patient support apparatus whether is docked with or undocked from the magnetic resonance tomography system, actuation of the first and second actuation facilities results either in the coupling or uncoupling of the patient support apparatus to/from the magnetic resonance tomography system or the raising or lowering of a patient support plate of the patient support apparatus. Essential components for docking or undocking or for the vertical adjustment of the patient support plate are integrated in a hydraulic unit.

13 Claims, 2 Drawing Sheets

PATIENT SUPPORT APPARATUS

CROSS REFERENCE TO RELATED APPLICATIONS

This application claims priority of German application No. 10 2009 042 873.9 filed Sep. 24, 2009, which is incorporated by reference herein in its entirety.

FIELD OF THE INVENTION

The invention relates to a mobile patient support apparatus to be connected in a releasable manner to a medical device.

BACKGROUND OF THE INVENTION

When patients are examined in an imaging system having a gantry, such as a computed tomography system, a magnetic resonance tomography system or a PET system, the patient has to be supported in the gantry. To this end the patient is positioned on a patient support plate, which can be moved into the gantry. The spatial extension of the gantry—typically in the form of a hollow cylinder with an external diameter of approx. 2 m—means that the patient support plate has to be at a distance of between 70 and 90 cm from the ground to be moved into the gantry. For the patient to be able to climb easily onto the patient support plate beforehand however, a distance of 55 cm from the ground should not be exceeded. Vertically adjustable patient support apparatuses are therefore now widely used with imaging systems with larger gantries.

An optimum workflow, in particular when immobile patients are supported, can be achieved when the patient support apparatus can be undocked, i.e. released, from the medical device and can also be operated in a mobile manner. This option is particularly important when the medical device is an imaging system operated according to the magnetic resonance principle, for example magnetic resonance tomography system or a magnetic resonance PET system. The extremely strong magnetic field active in the examination region means that the patient cannot be moved directly into the examination space using the normal patient support apparatuses used for hospital transportation (e.g. patient couch, trolley, hospital bed, etc.). With a patient support apparatus that can be docked and undocked, i.e. a patient support apparatus that can be connected in a releasable manner to the medical device, the patient can be safely transferred for example from a hospital bed to the patient support apparatus that can be connected to the medical device in a magnetic field-free space (preparation space). To this end the mobile undockable patient support for connection to a magnetic resonance tomography system must be designed to be sufficiently non-magnetic so that it is not attracted by the magnet in its leakage field. It is also advantageous if the mobile patient support apparatus can also be adjusted vertically in the undocked state, in particular being able to be adjusted to the level of a hospital bed, to facilitate the transfer of an immobile patient. A low overall weight of the patient support apparatus is also an important prerequisite for mobile deployment.

Numerous patient support apparatuses with vertically adjustable patient support plates are known in medical engineering. They are generally fitted with electric or hydraulic lifting systems. Electric lifting systems are generally moved by a spindle drive with an electric motor. They can generally only be adjusted by means of this motor and have to be accompanied by an energy storage unit (battery or accumulator) when deployed in a mobile manner. Hydraulic lifting systems are generally moved by a lifting piston, into which pressurized hydraulic oil is fed. They provide an efficient means of manual adjustment by means of foot pedals in conjunction with a piston pump.

A patient support apparatus is known from patent publication DE 42 24 695 C1, in which a hydraulic pump is driven by an electric motor.

A mobile patient support apparatus is known from publication EP 0 209 326 A2, in which manual vertical adjustment by means of foot pedals in conjunction with a piston pump is possible in the undocked state. A further hydraulic pump is present for automatic vertical adjustment in the docked state, this pump being driven by way of a hydraulic motor disposed outside the patient support apparatus.

SUMMARY OF THE INVENTION

The object of the present invention is to simplify a mobile, vertically adjustable patient support apparatus and in particular its operation.

This object is achieved by a mobile patient support apparatus with the features according to the claims.

The mobile patient support apparatus according to the invention comprises a movable frame, to which a vertically adjustable patient support plate is fastened. Vertical adjustment takes place by means of a hydraulic lifting system. This comprises at least one hydraulic pump, a drive means to drive the hydraulic pump and a lifting cylinder. For the purposes of vertical adjustment the patient support apparatus furthermore comprises a number of manually actuatable actuation facilities, the manual actuation of a first actuation facility serving to raise and the manual actuation of a second actuation facility serving to lower the patient support plate. Switches for switching a drive motor for the hydraulic pump on and off for example are provided as actuation facilities. The actuation facilities are however preferably configured for actuation by a foot of the user. According to one advantageous embodiment of the invention a first actuation facility configured as a foot pedal likewise serves as a drive means for the hydraulic pump, in that the hydraulic pump is manually driven directly by the actuation. It is advantageously configured as a piston pump for this purpose. The patient support plate is thus raised by a pumping movement of the foot pedal in question.

The patient support plate is lowered by actuation of the second actuation facility. A motor drive can also be dispensed with here, in that actuation opens a valve for example with the patient support plate being lowered due to gravity.

The second actuation facility is also preferably configured as a foot pedal and according to one embodiment is likewise connected to a piston pump. Actuation of the second actuation facility then causes a control valve to open hydraulically, so that gravity causes hydraulic oil to flow out of the lifting cylinder to lower the patient support plate. Alternatively a second piston pump could also be dispensed for lowering purposes as long as a mechanical connection is present between the actuation facility and the control valve to actuate the control valve.

To dock the patient support apparatus with the medical device both the patient support apparatus and the medical device feature mutually compatible docking facilities. The docking facility on the patient support apparatus and the docking facility on the medical device when brought together engage with one another in such a manner that the patient support apparatus is fastened and fixed to the medical device as a result and according to one preferred embodiment control of the patient support apparatus can also be brought about by the control system of the medical device. During the docking operation a plurality of electrical connections between the patient support apparatus and the medical device are established for this purpose for example. The docking of the patient support apparatus according to the invention with a medical device takes place essentially in two steps here:

First the mobile support apparatus is pushed onto the medical device in such a manner that the docking facility on the patient support apparatus and the compatible docking facility on the medical device engage correctly. In this process, when the two docking facilities are brought together, a contact element present on the docking facility of the patient support apparatus brings about a switching of the functions carried out with the actuation facilities.

In the second step the patient support apparatus is actually fastened and fixed to the medical device. Whereas during mobile operation of the patient support apparatus the two actuation facilities bring about the raising and lowering of the patient support plate, once they have been brought together, actuation of the first actuation facility causes the two docking units to be connected to one another by way of a coupling, for example a hydraulically actuatable claw coupling. This establishes a rigid mechanical connection between the patient support apparatus and the medical device. The coupling can likewise bring about the reliable closing of any electrical contacts present between the medical device and the patient support apparatus.

The patient support apparatus and the medical device can only be separated from one another again when the coupling has been released. Release of the coupling is brought about by an actuation of the second actuation facility. Once the coupling has been released, the patient support apparatus can be pulled away from the medical device. Only when the two docking facilities have been separated from one another again and the contact element no longer has contact with the medical device is the original function of the actuation facilities restored when raising and lowering the patient support plate.

The patient support apparatus features a control facility to switch between the different functions that are performed by actuation of the actuation facilities. It comprises at least the contact element and two control valves and, when the first actuation facility is actuated, causes the patient support plate to be raised, as long as the contact element has no contact with the docking facility of the medical device, or, if there is contact, causes the coupling to connect the medical device and the patient support apparatus to be actuated and the patient support apparatus and the medical device to be coupled together. With regard to the second actuation facility, its actuation without contact between the contact element and the docking facility of the medical device results in the lowering of the patient support plate and, if there is contact, the release of the coupling.

The invention has the advantage that the switching of the respective function of the actuation facilities with two actuation facilities allows four functions (raising, lowering, coupling, uncoupling) to be executed. This reduces the complexity of the patient support apparatus and simplifies its operation.

The actuation facilities of the patient support apparatus according to the invention are preferably configured as pedals (foot pedals). However other actuation facilities, for example manually actuatable levers, switches, etc, are possible. A hydraulic pump, in particular a piston pump, connected mechanically to an actuation facility allows relatively strong forces brought about by the user manually with relatively little force expenditure to act at the hydraulic actuators (lifting cylinder, claw coupling), as required to raise the patient support plate or for coupling purposes.

The second actuation facility is also advantageously connected to a hydraulic pump, preferably a piston pump, which brings about the lowering of the patient support plate or the release of the coupling. Alternatively however actuation of the second actuation facility can also directly open a valve so that actuation in the undocked state causes the patient support plate to be lowered—due to gravity—and in the docked state causes the coupling to be released—for example due to spring force. There is therefore no need for a piston pump to lower the patient support plate or to open the coupling.

In one embodiment of the invention in addition to at least one manually actuatable hydraulic pump the patient support apparatus also comprises at least one hydraulic pump, which can be motor driven. This allows automatic operation of the patient support apparatus in the docked state, in which the patient support apparatus is connected to the energy supply of the medical device. The patient support plate can thus be raised automatically for example, i.e. without manual actuation of the foot pedals. Control can take place here for example by way of the controller of the medical device or by way of switches present on the patient support apparatus.

The motor-operated hydraulic pump is preferably configured as a gear pump, which can be connected directly, i.e. without the intermediate connection of a transmission, to the motor, preferably an electric motor. This allows optimum overall efficiency to be achieved, allowing a high revolution electric motor with a small structural volume and very small magnetically active mass to be deployed.

The patient support apparatus, which can be operated by an electric motor, advantageously also comprises an energy storage unit (battery or accumulator) to supply voltage to the electric motor. Motor-driven raising and lowering of the patient support plate is therefore also possible when the patient support apparatus is operated in a mobile manner. Manual raising and lowering of the patient support plate by actuation of the foot pedals is therefore only necessary if automatic operation fails.

Components of the inventive patient support apparatus are advantageously integrated in a hydraulic unit. Only MR-compatible, non-magnetic materials are preferably used here as far as possible. The hydraulic unit advantageously comprises at least one piston pump, control valves and a hydraulic oil container. If a further piston pump is also present to lower the patient support plate and/or to release the claw coupling, this is preferably also integrated in the hydraulic unit. In the case of a patient support apparatus that can also be operated by electric motor the electric motor and connected pump are also preferably contained in the hydraulic unit. Substantial integration of the components in the hydraulic unit reduces both cost and weight. The hydraulic unit is preferably disposed in a region of the patient support apparatus facing away from the medical device in the docked state of the patient support apparatus.

With the hydraulic unit according to the invention the orientation of the electric motor is not subject to normal restrictions, like the bearings for coupling to and uncoupling from a transmission system. Therefore when an electric motor is used, it is preferably disposed within the patient support apparatus in such a manner that the leakage field of the magnet of the magnetic resonance tomography system does not subject the couch to any relevant forces in the uncoupled state and in the coupled state the leakage field of the magnet acting on the motor remains small.

BRIEF DESCRIPTION OF THE DRAWINGS

The invention is described in more detail below with reference to an exemplary embodiment. In the drawings.

DETAILED DESCRIPTION OF THE INVENTION

Figure 1:
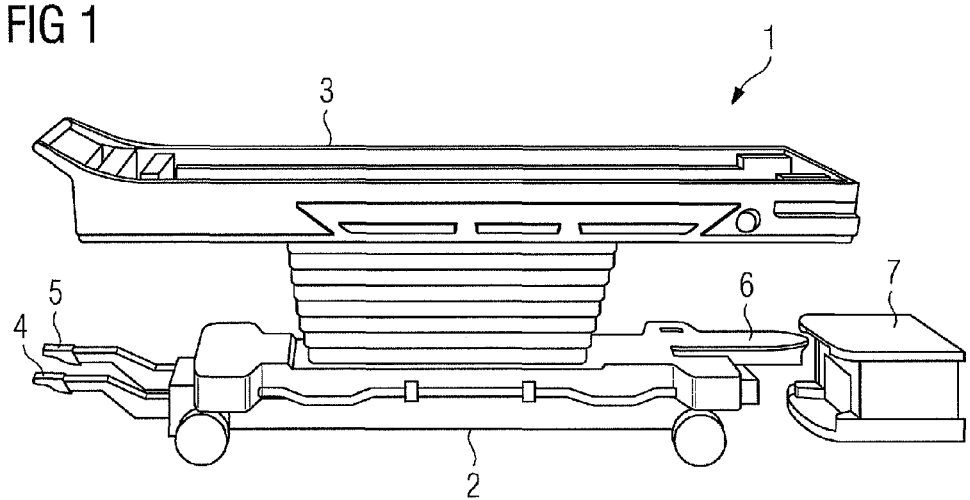
FIG. 1 shows a mobile patient support apparatus according to the invention.

FIG. 1 shows a patient support apparatus in the form of a mobile patient couch 1 according to the invention. It comprises a movable frame 2, to which a vertically adjustable patient support plate 3 is fastened. Vertical adjustment takes place by means of a hydraulic unit, shown in more detail in FIG. 2. For manual vertical adjustment during mobile operation of the patient couch 1, it comprises in particular the two foot pedals 4 and 5, which are each connected directly in a mechanical manner to a piston pump. Manual actuation of the one foot pedal 4 causes hydraulic oil to be pumped into a lifting cylinder to raise the patient support plate. To lower it, actuation of the other foot pedal 5 causes hydraulic oil to be discharged from the lifting cylinder.

A docking facility 6 is located at an end of the frame 2 opposite the foot pedals 4, 5. It is compatible with a docking facility 7 of a medical device (not shown), in particular of a magnetic resonance tomography system. To connect the patient couch 1 in a releasable manner to the medical device the patient couch 1 is brought up to the medical device in such a manner that the docking facilities 6 and 7 engage with one another.

Figure 2:
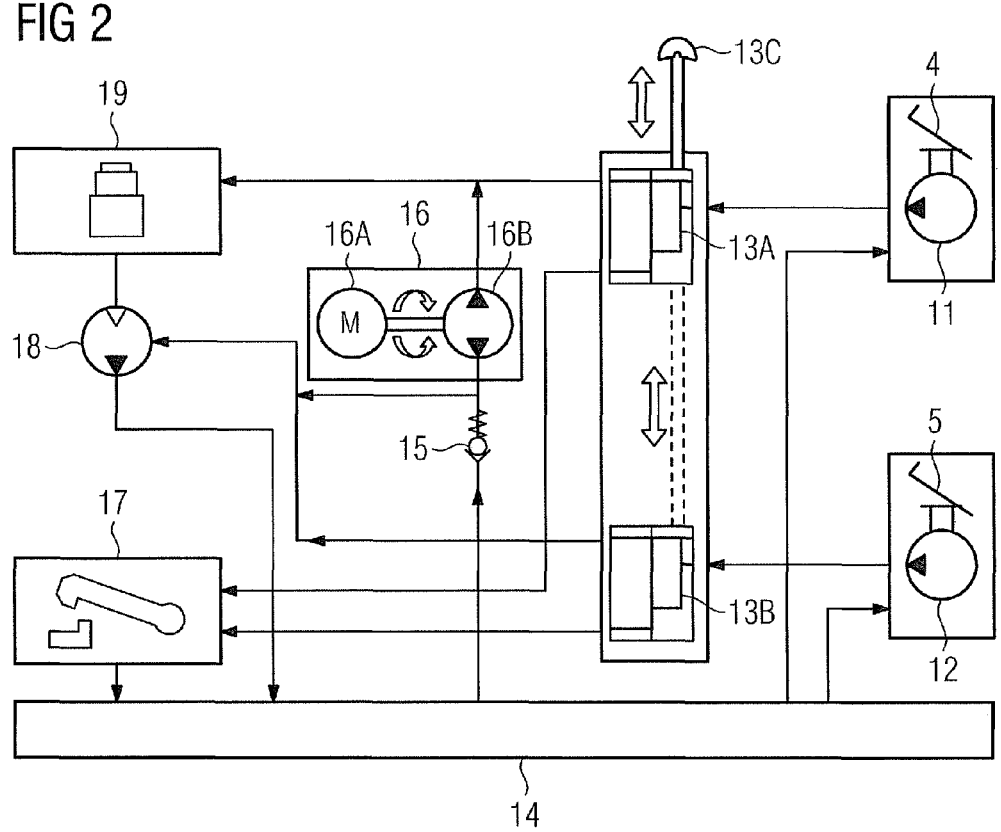
FIG. 2 shows a block circuit diagram of a hydraulic unit of a mobile patient support apparatus according to the invention and FIG. 3 shows an integrated hydraulic unit.

FIG. 2 shows a highly simplified block circuit diagram of the hydraulic unit of a patient support apparatus according to the invention. Parts that are not important in respect of the invention, for example non-return valves or overflow valves required for safe operation, are not shown.

The patient couch 1 is initially in mobile operation, i.e. in the undocked state. Pressing on the foot pedal 4 (see also FIG. 1) actuates the piston pump 11. This causes hydraulic oil to be pumped out of a hydraulic oil container 14 by way of a control valve 13A into a lifting cylinder 19, which is extended as a result, thereby raising the patient support plate 3 (see FIG. 1). Conversely pressing on the foot pedal 5 actuates the piston pump 12, with the result that hydraulic oil flows by way of a hydraulically controllable control valve 13B out of the lifting cylinder 19 into the hydraulic oil container 14 and the patient support plate 3 is lowered.

When the patient couch is docked with the medical device, the docking facility 6 of the patient couch 1 and the docking facility 7 of the medical device are first brought together correctly. In this process a contact pin 13C of a control facility 13 is actuated and the two control valves 13A and 13B are switched from a first valve position to a second valve position. In the second valve position (not shown) actuation of the foot pedal 4 and thus the piston pump 11 causes a claw coupling 17 to close and therefore the patient couch to be coupled to the medical device. In the process the hydraulic force transfer allows the easy transfer of forces to close the claw coupling 17, as required for precise centering of the patient couch 1 on the medical device, the connection of electrical contacts to supply voltage to the couch and the connection of signal contacts to transfer measurement data. After coupling the patient couch 1 is connected rigidly to the medical device.

The patient couch 1 can only be released from the medical device again after the patient couch 1 has been uncoupled from the medical device. This is done by means of the piston pump 12 as a result of actuation of the foot pedal 5. Only when the claw coupling 17 has been uncoupled again can the patient couch 1 be released, i.e. undocked, from the medical device. After undocking there is no longer any contact between the contact pin 13C and the medical device, so the control valves 13A and 13B return automatically to the first valve position (for mobile operation). The return can be effected by means of spring force for example.

As well as manual adjustment of the lifting cylinder 19 the hydraulic unit according to the exemplary embodiment also offers possibilities for automatic adjustment by means of an electric motor/pump unit 16. An electric motor 16A here drives a gear pump 16B directly, preferably without intermediate connection of a transmission. The gear pump 16B pumps hydraulic oil into the lifting cylinder 19. An inadvertent return flow of hydraulic oil into the hydraulic oil container 14 is prevented by a non-return valve 15. The patient support plate is let down by the pump 16B running backward and allowing hydraulic oil from the lifting cylinder 19 to flow back into the hydraulic oil container 14 by way of a control valve 18. The weight of the patient support plate is utilized here. The lowering speed is adjusted and kept almost constant by means of a flow limiting valve (not shown).

The patient couch 1 is preferably operated by electric motor in the docked state, in that the electric motor 16A is connected electrically to the voltage supply and controller of the medical device. The patient couch 1 is then controlled by way of the control facility of the medical device, the control valve 18 bring blocked, once the patient support plate 3 has reached its insertion height. The patient support plate 3 then maintains the set height. A horizontal drive of the patient support plate 3 is then activated. At the same time the piston pump 12 is blocked, to prevent undocking, as long as the patient support plate 3 has left its initial position.

If it is also to be possible to adjust by means of electric motor during mobile operation, the patient couch 1 must also have a battery or accumulator (not shown).

Figure 3:
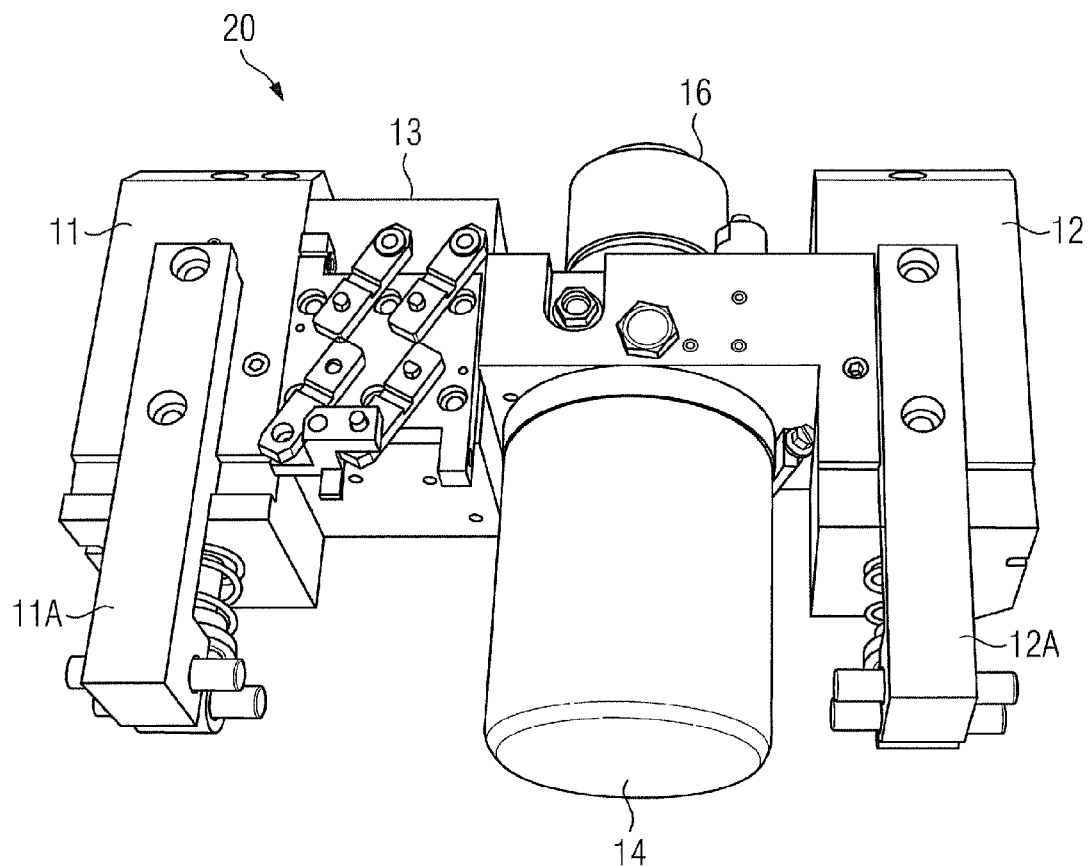

One preferred embodiment of the invention is shown in FIG. 3. Here the integrated hydraulic unit 20 comprises the two piston pumps 11 and 12, on which holders 11A and 12A are provided for the attachment of foot pedals (not shown in FIG. 3). The hydraulic unit 20 also comprises the control unit 13, which features two control valves. Actuation of the piston pumps 11 and 12 results—depending on the position of the control valves—either in the actuation of the lifting cylinder 19 or the claw coupling 17 of the patient couch 1. The hydraulic oil container 14 is also integrated in the hydraulic unit 20.

The hydraulic unit 20 according to the exemplary embodiment further comprises the motor/pump unit 16, which comprises a compact, high revolution electric motor (up to 5000 rpm) and a gear pump connected directly thereto—in other words without intermediate connection of a transmission. Since the electric motor only operates uninterrupted for a few seconds to raise the patient, a suitable thermal overload monitor for the motor allows a very compact model to be selected, which only has a very small overall magnetic mass.

The components of the hydraulic unit 20 are advantageously integrated in milled aluminum blocks. The gear pump 16A with the attached motor 16A, the piston pumps 11 and 12 and control and non-return valves are therefore present in milled aluminum blocks. The hydraulic connecting lines between the components are also integrated in the milled aluminum blocks, so that no external hoses or lines are required between the components.

The described electrohydraulic system has for example the following advantages:

Optimum ratio of available drive power to structural volume of the electric drive due to low-loss hydraulic transfer.

Optimum overall efficiency due to direct transmission-free coupling of the high revolution electric motor to the hydraulic unit and thus optimum ratio of available drive power to motor weight, in particular with regard to the proportion by weight of magnetic structural materials. The position of the electric motor can largely be freely selected within the patient couch, as the orientation of the motor can be selected independently of transmission couplings. In the case of magnetic resonance tomography systems the motor should be disposed so that whatever the position of the patient support apparatus in relation to the magnet of the magnetic resonance tomography apparatus, the biggest possible distance can always be maintained between electric motor and magnet, for example by selecting a position close to the ground in the center of the movable frame.

Minimum overall weight of the mechanical components and in particular of the hydraulic components due to their integration in a hydraulic unit and preferably substantial execution in aluminum.

Allows a non-magnetic implementation by using substantially integrated hydraulic functional parts using aluminum block technology.

Low-cost solution.

Allows both electrically assisted operation and manual adjustment by means of pedals, so that vertical adjustment is also possible in the uncoupled state. The patient can therefore be transferred comfortably to a hospital bed at any time, regardless of the charge state of a battery, which would have to be carried along for the purely electrical operation of the vertical adjustment system.

The integration of hydraulic control functions means that it is possible to control both the vertical adjustment and the docking and undocking of the patient support apparatus. In this process manual operation of the vertical adjustment system is released when the patient support apparatus is undocked from the medical device.

The dual function of the pedals, whereby, when the patient support apparatus is moved onto the medical device, the pedals are used for docking and undocking, while in mobile operation they are used to raise or lower the patient support plate, reduces the overall weight.

The invention claimed is:

1. A mobile patient support apparatus to be connected in a releasable manner to a medical device, comprising:
a movable frame;
a patient support plate that is adjusted vertically relative to the movable frame;
a hydraulic pump that vertically adjusts the patient support plate;
a first actuation device that actuates the hydraulic pump to raise the patient support plate;
a second actuation device that actuates the hydraulic pump to lower the patient support plate; and
a control device having a contact element that couples the entire mobile patient support apparatus to the medical device by actuating the first actuation device when the contact element is in contact with the medical device, and releases the entire mobile patient support apparatus from the medical device by actuating the second actuation device so that the contact element is not in contact with the medical device.

2. The patient support apparatus as claimed in claim 1, wherein the first and the second actuation devices are a first and a second foot pedals.

3. The patient support apparatus as claimed in claim 2, wherein the patient support apparatus comprises two hydraulic pumps and the first and the second foot pedals are drive devices for the two hydraulic pumps respectively.

4. The patient support apparatus as claimed in claim 3, wherein the hydraulic pump and/or the two hydraulic pumps are piston pumps.

5. The patient support apparatus as claimed in claim 3, wherein the patient support apparatus comprises a further hydraulic pump that is driven by a motor.

6. The patient support apparatus as claimed in claim 5, wherein the further hydraulic pump is a gear pump.

7. The patient support apparatus as claimed in claim 5, wherein the motor is an electric motor.

8. The patient support apparatus as claimed in claim 7, wherein the patient support apparatus comprises a battery or an accumulator to supply energy to the electric motor.

9. The patient support apparatus as claimed in claim 7, wherein the control device, the two hydraulic pumps, the further hydraulic pump, and the electric motor are an integrated hydraulic unit.

10. The patient support apparatus as claimed in claim 2, wherein the first and/or the second foot pedals are drive devices for the hydraulic pump.

11. The patient support apparatus as claimed in claim 1, wherein the medical device is a magnetic resonance tomography system.

12. The patient support apparatus as claimed in claim 1, further comprising a claw coupling that is closed by actuating the first actuation device and is open by actuating the second actuation device.

13. A method for connecting a mobile patient support apparatus to a medical device in a releasable manner, comprising:
providing a movable frame;
vertically adjusting a patient support plate relative to the movable frame by a hydraulic pump;
actuating the hydraulic pump by a first actuation device to raise the patient support plate;
actuating the hydraulic pump by a second actuation device to lower the patient support plate; and
coupling the entire mobile patient support apparatus to the medical device by actuating the first actuation device when a contact element of a control device is in contact with the medical device and releasing the entire mobile patient support apparatus from the medical device by actuating the second actuation device so that the contact element is not in contact with the medical device.

* * * * *